United States Patent
Park et al.

(10) Patent No.: US 6,190,690 B1
(45) Date of Patent: Feb. 20, 2001

(54) SUSTAINED/IMMEDIATE ACTING KETOPROFEN PATCH AND PROCESS FOR MANUFACTURING THE SAME

(75) Inventors: Chang-Kyu Park; Jae-Keun Choi; Kwang-Ho Lee; Byong-Chul Hyun; Yi-Dan Ha, all of Seoul (KR)

(73) Assignee: STC Corporation (KR)

( * ) Notice: Under 35 U.S.C. 154(b), the term of this patent shall be extended for 0 days.

(21) Appl. No.: 08/884,509

(22) Filed: Jun. 27, 1997

(30) Foreign Application Priority Data

Jul. 3, 1996 (KR) .................................................. 96-51525

(51) Int. Cl.⁷ ...................................................... A61F 13/02
(52) U.S. Cl. ........................... 424/449; 424/448; 602/41; 604/289; 604/304; 604/305; 604/307
(58) Field of Search ..................................... 424/449, 448; 602/41; 604/289, 304, 305, 307

(56) References Cited

U.S. PATENT DOCUMENTS 5,505,956 * 4/1996 Kim et al. .............................. 424/448
5,730,999 * 3/1998 Lehmann et al. ..................... 424/443

* cited by examiner

*Primary Examiner*—S. Mark Clardy
*Assistant Examiner*—Michael A. Williamson
(74) *Attorney, Agent, or Firm*—Cook, Alex, McFarron, Manzo, Cummings & Mehler, Ltd.

(57) ABSTRACT

A sustained/immediate acting ketoprofen patch. A moisture permeable backing, a moisture non-permeable primer, a moisture high-permeable drug layer containing ketoprofen and a skin adhesion layer controlling release of a drug solution are piled up. An ethyl acetate soluble acrylic/rubber adhesive is coated onto a silicon coated paper, dried and transfer coated onto the backing to form the primer. The drug layer is formed by coating a drug solution onto a silicon coated paper, drying and transfer coating onto the primer. The skin adhesion layer is formed by coating a mixture of a solution prepared by dissolving an emulsifier in ethyl acetate and acrylic adhesive, drying and transfer coating onto the drug layer. The ketoprofen patch has a drug release controlling function and a good adhesion strength. The drug transferring effect through the skin is good.

16 Claims, 2 Drawing Sheets

SUSTAINED/IMMEDIATE ACTING KETOPROFEN PATCH AND PROCESS FOR MANUFACTURING THE SAME

BACKGROUND OF THE INVENTION

1. Field of the Invention

The present invention relates to a ketoprofen patch appropriate in treating arthritis, and more particularly to a remedy containing ketoprofen, which is percutaneously administrated and has therapeutic effect on arthritis, rheumatism, etc.

2. Description of the Prior Art

Ketoprofen plaster (trade name; KETOTOP, Pacific Pharm. Co., Ltd.) sold at the market as an arthritis remedy which is percutaneously administrated, consists of non-woven fabric, poly(isobutylene) rubber adhesive as a primer, which is formed on the nonwoven fabric by transfer coating, and mixture of acrylic adhesive, ketoprofen as drug and propylene glycol monolaurate as an enhancer for helping permeation of the drug into skin, which is formed on the primer by transfer coating. Thus manufactured ketoprofen plaster rarely has any difference with the conventional PAS (para-aminosalicylic acid) agent.

U.S. Pat. No. 5,505,956 discloses a ketoprofen patch having 2–5 adhesion layers between a backing as a supporting material and a liner. In the ketoprofen patch, when a non-moisture-permeable backing is used, layers from the backing to a surface layer which is to be contacted with skin, consist of from a layer having a high moisture content to a layer having a low moisture content. On the contrary, when a moisture-permeable backing such as nonwoven fabric is used, layers from the backing to the surface layer which is to be contacted with the skin, consist of from a layer having a low moisture content to a layer having a high moisture content. In order to increase moisture content, the ketoprofen patch uses 0.3–30 wt % of poly(vinyl alcohol), and in each layer, 0.1–40 wt % of ketoprofen is mixed with acrylic adhesive and an enhancer such as propylene monoglycolate.

However, in the ketoprofen patch constructed as mentioned above, since ketoprofen drug exists as a mixture with the acrylic adhesive, even though solubility of ketoprofen is good, diffusion thereof is to be late. In addition, since the release amount of the drug can not be controlled, the amount of drug administered cannot be kept constant over of time. Further, since the ketoprofen which is pulverulent drug, or a non-adhesive type polymer such as the poly(vinyl alcohol) are mixed with the acrylic adhesive, the adhesion strength to the skin is so flimsy that re-attachment of the patch to the skin becomes difficult.

Particularly, because the patch is a medium for transferring drug through the skin, therapeutic effect is proportional to contacting area between the patch and the skin. Therefore, if the area of the patch peeled off from the skin is wide, the drug transferance rate decreases and accordingly, the therapeutic effect remarkably decreases.

Hence, development for a ketoprofen patch having a good adhesion strength for keeping therapeutic effect of drug for a long time, a constant drug release amount per unit time and a good initial drug release characteristic, is highly demanded in this technical field.

SUMMARY OF THE INVENTION

The present invention has thus been constructed to overcome one or more of the above described problems of the conventional art. Accordingly, it is an object of the present invention to provide a sustained/immediate acting ketoprofen patch which can control the drug release amount whereby therapeutic effect of the patch can be continuously and homogeneously or immediately kept.

Another object of the present invention is to provide a sustained/immediate acting ketoprofen patch having a good adhesion strength to skin whereby the therapeutic effect of the patch can sufficiently be transferred to the skin when the patch is attached to the skin, and attaching/detaching of the patch to/from the skin can be possible as occasion needs.

Still another object of the present invention is to provide a ketoprofen patch having a continuously constant drug release effect or a good initial drug release effect.

Yet another object of the present invention is to provide a method for rid manufacturing the above mentioned sustained/immediate acting ketoprofen patch.

To accomplish the object of the present invention, there is provided a sustained/immediate acting ketoprofen patch comprising: a backing; a non-moisture-permeable acrylic/rubber adhesive primer; a high-moisture-permeable drug layer in which ketoprofen is dissolved in water soluble polymer; and a skin adhesion layer capable of controlling release amount of a drug. Particularly, the ketoprofen patch has a complex laminated-structure in which the drug layer and an adhesive layer are completely separated.

In the present invention, the term, "non-moisture-permeable" means hardly permeating moisture, and the term of "high-moisture-permeable" means permeating moisture very well.

Methods for manufacturing the ketoprofen patches of the sustained type or the immediate acting type are similar but different only in employing materials according to the types.

The sustained ketoprofen patch from which drug is continuously released with the lapse of time is manufactured by a method comprising the steps of: (1) forming a primer by coating an acrylic adhesive dissolved in ethyl acetate onto a silicon coated paper or a polyester film, drying at 80° C. for 1–2 minutes (thickness of a coating layer is 20–50 µm), and then transfer coating onto a backing; (2) forming a drug layer by coating a drug solution prepared by adding ketoprofen dissolved in an enhancer to a mixture of an aqueous PVA and an adhesive of acrylic emulsion, and/or EVA emulsion, and/or synthetic rubber latex, onto a silicon coated paper, drying (thickness of a coating layer is 30–50 µm), and transfer coating onto the printer; and (3) forming a skin adhesion layer by dissolving an emulsifier in ethyl acetate to obtain a solution, mixing the solution with an acrylic adhesive, stirring the thus obtained mixture, coating onto a silicon coated paper, drying (thickness of coating layer is 5–40 µm, preferably 10–20 µm), and transfer coating onto the drug layer.

The immediate acting ketoprofen patch having a good initial release effect of drug is manufactured by another method comprising the steps of: (1) forming a primer by coating a rubber adhesive onto a silicon coated paper or polyester film, drying at 60° C. for 1–2 minutes and at 80° C. for 1 minute (thickness of coating layer is 20–50 µm, preferably 30–40 µm), and transfer coating onto a moisture-permeable backing; (2) forming a drug layer by coating a drug solution prepared by mixing ethylene-vinyl acetate copolymer emulsion and/or synthetic rubber latex in aqueous PVA, and adding ketoprofen dissolved in an enhancer, onto a silicon coated paper, dying (thickness of coating layer is 10–100 µm, preferably 30–40 µm), and transfer coating onto the primer; (3) forming a skin adhesive layer by dissolving emulsifier in ethyl acetate to obtain a solution, mixing the solution with an acrylic adhesive, stirring the mixture, coating onto a silicon coated paper, drying (thickness of coating layer is 5–40 μm, preferably 10–20 μm), and transfer coating onto the drug layer.

The immediate acting ketoprofen patch according to the present invention can maximally restrain a reverse diffusion of the drug and the enhancer to the primer, through action of the rubber adhesive contained in the primer, and can accomplish the smooth release of the drug by increasing hydrophobicity of the drug layer by adding the EVA or the synthetic rubber latex to a water soluble polymer.

Most of the percutaneous absorbable agent is, except a type having drug layer of liquid phase such as reservoir type or hydrogel type, used polymer having adhesion or adhesive property as a binder in case of a matrix type having a drug layer of solid phase such as the present invention. However, in the present invention, a binder having no adhesion or adhesive property can be used, so that selection range of the binder becomes broad.

BRIEF DESCRIPTION OF THE DRAWINGS

The above objects, and other features and advantages of the present invention will become more apparent by describing in detail preferred embodiments thereof with reference to the attached drawings, in which.

DETAILED DESCRIPTION OF PREFERRED EMBODIMENT

Hereinafter, preferred embodiments of the present invention will be explained in greater detail with reference to the accompanying drawings.

Figure 1:
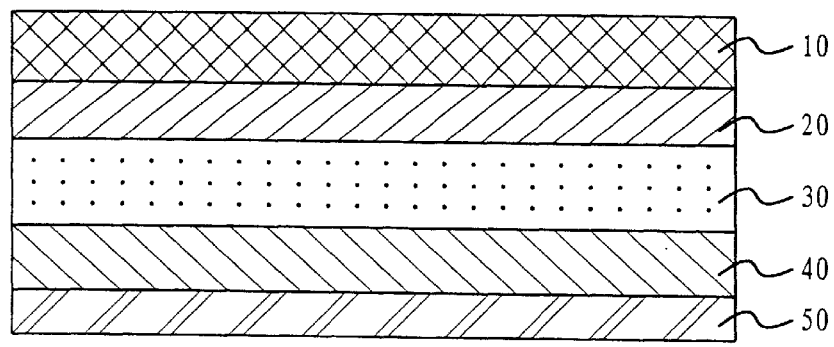
FIG. 1 is a cross-sectional view of a sustained/immediate acting ketoprofen patch in accordance with an embodiment of the present invention.

FIG. 1 is a cross-sectional view of a sustained/immediate acting ketoprofen patch in accordance with an embodiment of the present invention. Referring to FIG. 1, the ketoprofen patch is formed by successively laminating a backing 10, a primer 20, a drug layer 30, a skin adhesion layer 40 and a separate liner 50.

For the backing 10, nonwoven fabric, polyester film or polyurethane film, each of which may be moisture-permeable or non-moisture-permeable, can be used. However, it is most preferable to use the moisture-permeable nonwoven fabric.

The primer 20 is provided for preventing drug and enhancer contained in the drug layer 30 from leaking to the backing 10 or primer 20, or out of the backing 10. In order to impart continuous drug release characteristic to the primer 20, acrylic adhesive which can be dissolved in ethyl acetate is used. By this, the drug can be reverse diffused, whereby concentration and diffusion of the drug can be controlled and thus drug release is controlled.

For improving an initial drug release characteristic, a rubber adhesive is used. The rubber adhesive is made by adding a tackifier such as terpenes and an antioxidant, to rubber. In this case, reverse diffusion of the drug is minimized. That is, the primer 20 is formed by coating the adhesive onto a silicon coated paper or a polyester film and then drying. An appropriate thickness of the coating layer is 20–50 μm, and the primer 20 acts as adhesive between the backing 10 and drug layer 30.

For a maximum drug content and a maximum release effect, the drug layer 30 desirably employs a mixed matrix of non-adhesive and water soluble polymer and water non-soluble polymer. In addition, it is preferable to use an enhancer which can dissolve the ketoprofen drug which is soluble in oil and insoluble in water. For the enhancer, lipid acid alcohol, sorbitan monooleate, poly(ethleneglycol), glycerin, pyrrolidone, N-methyl pyrrolidone, dimethyl formamide, dimethyl sulfoxide or diethyl toluamide can be used. At this time, 1 g of the enhancer can effectively dissolve 1 g of the powder of the ketoprofen drug within 15 minutes. Herein, lipid acid alcohol is at least one selected from the group consisting of oleyl alcohol and a derivatives thereof. In case mixture of oleyl alcohol and sorbitan monooleate is used as an enhancer, a mixing ratio is 10:90–90:10 by weight parts and preferably of 30:70–70:30 by weight parts. Ketoprofen is typically contained by 1–90 wt %, preferably 10–20 wt % based on the drug solution.

As for the polymer of the matrix, a water soluble polymer is at least one selected from the group consisting PVA, poly(acrylic acid), poly(acryl amide), poly(N-vinyl pyrrolidone), chitin, chitosan, cellulose and salt thereof, preferably PVA. A water non-soluble polymer is selected from the group consisting acrylic adhesive, EVA and synthetic rubber latex. In the present invention, mixed matrix of water soluble polymer and water non-soluble polymer is used. A mixture of PVA and the acrylic adhesive, or a mixture of PVA with EVA and/or synthetic rubber latex (preferably SBR(Stylene-butadiene rubber)) can be used.

In the case of using the acrylic adhesive, the mixing ratio of PVA and the solid content of the acrylic adhesive is 10:90–90:10 by weight parts, and preferably 50:50–75:25 by weight parts. Amounts of mixture PVA and acrylic adhesive is 5–95 wt % based on the drug solution. In case of using EVA, the mixing ratio of PVA and the solid content of EVA is 10:90–90:10 by weight parts, and preferably 30:70–70:30 by weight parts. Amounts of mixture PVA and EVA is 10–80 wt % based on the drug solution. Further, in the case of using synthetic rubber latex, the mixing ratio of PVA and the solid content of synthetic rubber latex is 10:90–90:10 by weight parts, and preferably 25:75–75:25 by weight parts. Amounts of mixture PVA and synthetic latex is 10–80% based on the drug solution.

In the case of using EVA and synthetic rubber latex, the mixing ratio of PVA, EVA and synthetic rubber latex is 10–90:10–90:1–50 by weight parts. Amount of mixture PVA, EVA and synthetic rubber latex is 10–80 wt % based on the drug solution. At this time, EVA having ethylene content of 1–99 wt %, and preferably 10–50 wt %, is used. In addition, the drug dissolved solution is used after adjusting the amount of the solution to be 10–90 wt %, and preferably 50–70 wt % based on the total drug layer.

These mixed matrix of a water soluble and non-soluble polymer and drug solution prepared by dissolving ketoprofen in enhancer are coated on a silicon coated paper or a polyester film. Then, the mixing ratio of enhancer and ketoprofene is 100:1–50 by weight parts. The thickness of the coated layer after the drying is preferably 30–50 μm.

If the thickness of skin adhesion layer 40 is thickened only for improving the adhesion to the skin, a lag time for the release of the drug is lengthened. That is, if the thickness of the skin adhesion layer 40 is set to 40 μm or over for improving the adhesion and/or hold strength, then drug release becomes difficult. If the thickness of the skin adhesion layer 40 is set to 5 μm or less, the adhesion or holding strength to the skin is decreased. Accordingly, although the initial adhesion is good, the layer is liable to be detached during the activity of the user. Accordingly, for the strong adhesion of the patch to the skin and for the constant release of the drug, the thickness of skin adhesion layer 40 is set to 5–40 μm and preferably 10–20 μm.

In the skin adhesion layer 40, mixture of acrylic adhesive layer and enhancer such as organic salt or emulsifier is used. This amounts is 0.005–50 wt % based on the drug layer. In case of using salt, amounts is 0.05–0.5 wt %. As for an organic salt, the moisture transpired from the skin dissolves the salt to provide a constant and minute passage in the polymer structure of the skin adhesive layer without decreasing the adherence to the skin. Accordingly, a constant amount of the drug can be released during a constant time. As for the emulsifier, oleyl alcohol, sorbitan monooleate, poly(ethylene glycol), glycerin, pyrrolidone, N-methyl pyrrolidone, dimethyl formamide, dimethyl sulfoxide or diethyl toluamide can be used. The preferred amount of the emulsifier is 5–10 wt % based on the skin adhesion layer for obtaining an increased solubility to the drug and for obtaining the constant release effect of the drug during a constant time without decreasing the adhesion strength.

The present invention will be described in more detail with reference to the following examples. However, the scope of the present invention according to the claims is not limited to the following examples.

EXAMPLE 1

Manufacturing of a sustained ketoprofen patch 1

A. Forming a primer (1) Acrylic adhesive dissoluble in ethyl acetate and having 55% of a solid content (trade name: ST-96, manufacturer: Suttong Co., Ltd.) was coated on a silicon coated paper and dried at 80° C. for 90 seconds. The thickness of the coating layer after the drying was 40 μm.

(2) The product obtained through the step of (1) was transfer coated onto a moisture permeable nonwoven fabric using a press roll to form a primer.

B. Forming a drug layer containing ketoprofen (1) 1 g of PVA 500 of degree of polymerization and 4 g of water were mixed and slowly stirred to obtain 20% of PVA aqueous solution (at this time, if PVA having a 1500 of degree of polymerization was used, 7 wt % of aqueous solution at the most, could be obtained). 4.71 g of the PVA aqueous solution and 1.57 g of acrylic emulsion adhesive having 55% of a solid content (trade name: ST-96-E, manufacturer: Suttong Co., Ltd.) was homogeneously mixed.

(2) 0.5 g of ketoprofen powder was mixed with 0.45 g of oleyl alcohol, and was dissolved through stirring.

(3) The products obtained through the steps of (1) and (2) and 1.65 g of sorbitan monooleate were mixed and stirred for 10 minutes to prepare a drug solution. This solution was coated on a silicon coated paper to the thickness of the coating layer of 50 μm. Then the coating layer was transfer coated on the primer manufactured by the above step A using a press roll to form a drug layer.

C. Forming a skin adhesion layer (1) 0.9 g of Bile salt was dissolved in 7.5 g of ethyl acetate. Thus obtained solution was mixed with 30 g of acrylic adhesive (trade name: ST-96, manufacturer: Suttong Co., Ltd.) and stirred. Thus obtained mixture was coated on a silicon coated paper and dried. The thickness of the coating layer was 30 μm.

(2) The product obtained through the step of (1) was transfer coated on the drug layer manufactured by the above step B using a press roll to form a skin adhesion layer.

EXAMPLE 2

Manufacturing of a sustained ketoprofen patch 2

A primer and a drug layer were manufactured using the same components and by the same methods described in Example 1. A skin adhesion layer was manufactured by the following method and was transfer coated onto the drug layer to form a ketoprofen patch.

Forming the skin adhesion layer: 0.18 g of sorbitan monooleate and 7.5 g of ethyl acetate were added to 0.72 g of oleyl alcohol and dissolved. The solution was mixed with 30 g of acrylic adhesive (trade name: ST-96, manufacturer: Suttong Co., Ltd.) and stirred. The mixture was coated on a silicon coating paper and dried at 60° C. for 1 minute, and then at 120° C. for 5 minutes. The thickness of the coating layer was 10 μm.

EXAMPLE 3

Manufacturing of an immediate acting ketoprofen patch 1

A. Forming a primer (1) 100 g of natural rubber, 120 g of a tackifier such as terpenes and 1 g of an common antioxidant (BHT, 2, 6-di-t-butyl-p-cresol) for a rubber were mixed and stirred in toluene so that a solid content therein became 30%. Thus obtained product was coated on a silicon coated paper and dried at 60° C. for 1 minute and at 80° C. for 1 minute. The thickness of the coating layer was 40 μm.

(2) A primer was formed by transfer coating the product obtained through the step of (1) onto a nonwoven fabric using a press roll.

B. Forming a drug layer containing ketoprofen (1) 1.5 g of PVA having a 500 of degree of polymerization and 6 g of water were mixed and slowly stirred to obtain 20% of PVA aqueous solution. 6.6 g of the PVA aqueous solution and 2.2 g of EVA emulsion having 55% of a solid content (trade name: 201, manufacturer: Suttong Co., Ltd.) were homogeneously mixed.

(2) 0.81 g of ketoprofen powder, 1 g of oleyl alcohol and 2 g of sorbitan monooleate are mixed and dissolved.

(3) The products obtained through the steps of (1) and (2) were mixed and stirred for 10 minutes to prepare a drug solution. The solution was coated on a silicon coated paper and dried at 70° C. for 6 minutes to the thickness of the coating layer of 36 μm Then the coating layer was transfer coated on the primer using a press roll to form a drug layer.

C. Forming a skin adhesion layer (1) 0.18 g of sorbitan monooleate and 7.5 g of ethyl acetate were added to 0.72 g of oleyl alcohol and dissolved to obtain a solution. Thus obtained solution was mixed with 30 g of acrylic adhesive (trade name: ST-96, manufacturer: Suttong Co., Ltd.) and stirred. Thus obtained mixture was coated on a silicon coated paper and dried at 60° C. for 1 minute and then at 120° C. for 5 minutes. The thickness of the coating layer was 10 μm.

(2) The product obtained through the above step of (1) was transfer coated on the drug layer manufactured by the above step B, (3) using a press roll to form a skin adhesion layer.

EXAMPLE 4

Manufacturing of an immediate acting ketoprofen patch 2

A primer and a drug layer were manufactured using the same components and by the same methods described in Example 3. A skin adhesion layer was manufactured by the following method and was transfer coated onto the drug layer to form a ketoprofen patch.

Forming the skin adhesion layer: 0.9 g of Bile salt was dissolved in 7.5 g of ethyl acetate to obtain a solution. This solution was mixed with 30 g of acrylic adhesive (trade name: ST-96, manufacturer: Suttong Co., Ltd.) and stirred. The mixture was coated on a silicon coated paper and dried at 60° C. for 1 minute, and then at 120° C. for 5 minutes, The thickness of the coating layer was 10 μm.

EXAMPLE 5

Manufacturing of an immediate acting ketoprofen patch 3

(1) 1 g of PVA having a 500 of degree of polymerization and 4 g of water were mixed and slowly stirred to obtain 20% of PVA aqueous solution. 2.2 g of the PVA aqueous solution and 6.6 g of EVA emulsion having 55 % of a solid content were homogeneously mixed.

(2) 0.81 g of ketoprofen powder was mixed with 1 g of oleyl alcohol and 2 g of sorbitan monooleate, and was dissolved.

(3) The products obtained through the steps of (1) and (2) were mixed and stirred for 10 minutes to prepare a drug solution. The solution was coated on a silicon coated paper and dried at 70° C. for 6 minutes to the thickness of the coating layer of 36 μm. Then, the coating layer was transfer coated onto the primer manufactured through example 3 and A, using a press roll to form a drug layer.

(4) The product manufactured through example 3, C, (1) was transfer coated onto the drug layer to obtain a skin adhesion layer.

EXAMPLE 6

Manufacturing of an immediate acting ketoprofen patch 4

(1) 100 g of SBR, 120 g of a tackifier such as terpenes and 1 g of an antioxidant (BHT) were mixed and stirred to dissolve the compounds so that a solid content therein became 30%. Thus obtained product was coated on a silicon coated paper and dried at 60° C. for 1 minute, and at 80° C. for 1 minute. The thickness of the coating layer was 40 μm.

(2) A primer was formed by transfer coating the product obtained through the step of (1) onto a nonwoven fabric using a press roll.

(3) The product obtained through example 3, B, (4) was transfer coated onto the primer to form a drug layer.

(4) The product obtained through example 3, C, (1) was transfer coated onto the drug layer to form a skin adhesion layer.

EXAMPLE 7

Manufacturing of an immediate acting ketoprofen patch 5

(1) 1 g of PVA having a 500 of degree of polymerization and 4 g of water were mixed and slowly stirred to obtain 20% of PVA aqueous solution. 2.8 g of the PVA aqueous solution, 2.8 g of EVA emulsion having 55% of a solid content (trade name: ST-96-E, manufacturer: Suttong Co., Ltd.) and 0.93 g of SBR latex having 48% of a solid content were homogeneously mixed.

(2) 0.81 g of ketoprofen powder was mixed with 1 g of oleyl alcohol and 2 g of sorbitan monooleate, and was dissolved.

(3) The products obtained through the steps of (1) and (2) were mixed and stirred for 10 minutes to prepare a drug solution. This solution was coated on a silicon coated paper and dried at 80° C. for 6 minutes to the thickness of the coating layer of 36 μm. Then, the coating layer was transfer coated onto the primer manufactured through example 3 and A, using a press roll to form a drug layer.

(4) The product manufactured through example 3, C and (1) was transfer coated onto the drug layer to obtain a skin adhesion layer.

EXAMPLE 8

Manufacturing of an immediate acting ketoprofen patch 6

(1) 2 g of PVA having a 500 of degree of polymerization and 8 g of water were mixed and slowly stirred to obtain 20% of PVA aqueous solution. 7.9 g of the PVA aqueous solution and 2 g of SBR latex were homogeneously mixed.

(2) 0.81 g of ketoprofen powder was mixed with 1 g of oleyl alcohol and 2 g of sorbitan monooleate, and was dissolved.

(3) The products obtained through the steps of (1) and (2) were mixed and stirred for 10 minutes to prepare a drug solution. This solution was coated on a silicon coated paper and dried at 70° C. for 6 minutes to the thickness of the coating layer of 36 μm.

(4) The coating layer obtained through the step (3) was transfer coated onto the primer manufactured through Example 1, A, using a press roll to form a drug layer.

(5) The product manufactured through Example 1, C, (1) was transfer coated onto the drug layer to obtain a skin adhesion layer.

COMPARATIVE EXAMPLE

Ketoprofen plaster (brand name: KETOTOP, manufacturer: Pacific Pharm. Co., Ltd.) sold at a market in this technical field was used.

Physical properties such as loading amount of drug per area, release amount of drug using a hairless mouse, drug release ratio per hour and adhesion strength to stainless steel were tested for the products manufactured by the examples according to the present invention and the ketoprofen plaster sold at a domestic market. The results are illustrated in Tables 1 and 2 and in FIGS. 2, 3 and 4.

TABLE 1

Comparison on the loading amount of drug and the adhesion strength

| physical property example | loading amount of drug (mg/1.8361 cm$^2$) | adhesion strength (g/cm) |
| --- | --- | --- |
| example 1 | 0.75 | 196 |
| example 2 | 0.75 | 195 |
| example 3 | 0.77 | 210 |
| example 4 | 0.77 | 193 |
| example 5 | 0.84 | 157 |
| example 6 | 0.77 | 204 |
| example 7 | 0.73 | 215 |
| example 8 | 0.71 | 230 |
| comparative example | 0.77 | 170 |

TABLE 2

Drug Release amount of drug using the hairless mouse

| time | exam. 1 | exam. 2 | exam. 3 | exam. 4 | exam. 5 | exam. 6 | exam. 7 | exam. 8 | com. exam. |
|---|---|---|---|---|---|---|---|---|---|
| 0 | 0.00 | 0.00 | 0.00 | 0.00 | 0.00 | 0.00 | 0.00 | 0.00 | 0.00 |
| 1 | 0.32 | 0.40 | 1.10 | 0.88 | 1.43 | 1.34 | 0.96 | 0.91 | 0.80 |
| 2 | 1.08 | 0.68 | 3.69 | 3.06 | 5.28 | 3.79 | 3.83 | 3.89 | 3.29 |
| 3 | 8.01 | 5.96 | 7.10 | 6.39 | 9.02 | 8.56 | 9.52 | 10.32 | 5.31 |
| 5 | 11.16 | 18.68 | 19.04 | 15.80 | 24.75 | 22.19 | 37.71 | 43.93 | 13.38 |
| 7 | 18.12 | 23.49 | 30.61 | 22.96 | 41.02 | 40.64 | 61.10 | 71.25 | 18.95 |
| 9 | 25.73 | 42.78 | 38.38 | 27.63 | 59.87 | 63.96 | 73.04 | 84.59 | 25.84 |
| 12 | 28.82 | 67.94 | 61.06 | 42.74 | 101.98 | 80.61 | 82.09 | 89.10 | 38.56 |
| 15 | | | 80.68 | 57.28 | 129.09 | 100.88 | 88.12 | 78.62 | 47.53 |
| 20 | | | 103.80 | 71.62 | 114.18 | 127.33 | 82.62 | 75.55 | 71.96 |
| 24 | | | 66.25 | 50.35 | 81.49 | 69.15 | 46.81 | 40.33 | 55.67 |

Note:
In table 2, exam. means example, and com. exam. means comparative example.

From the result of the test for the physical properties, ketoprofen patches manufactured by the examples according to the present invention have better release amounts of drug per hour when similar drug solutions were loaded and better adhesive strength to the skin than those of the conventional product (ketoprofen plaster: control), and keep continuous effect of the medicine for a long time, as shown in Tables 1 and 2.

Figure 2:
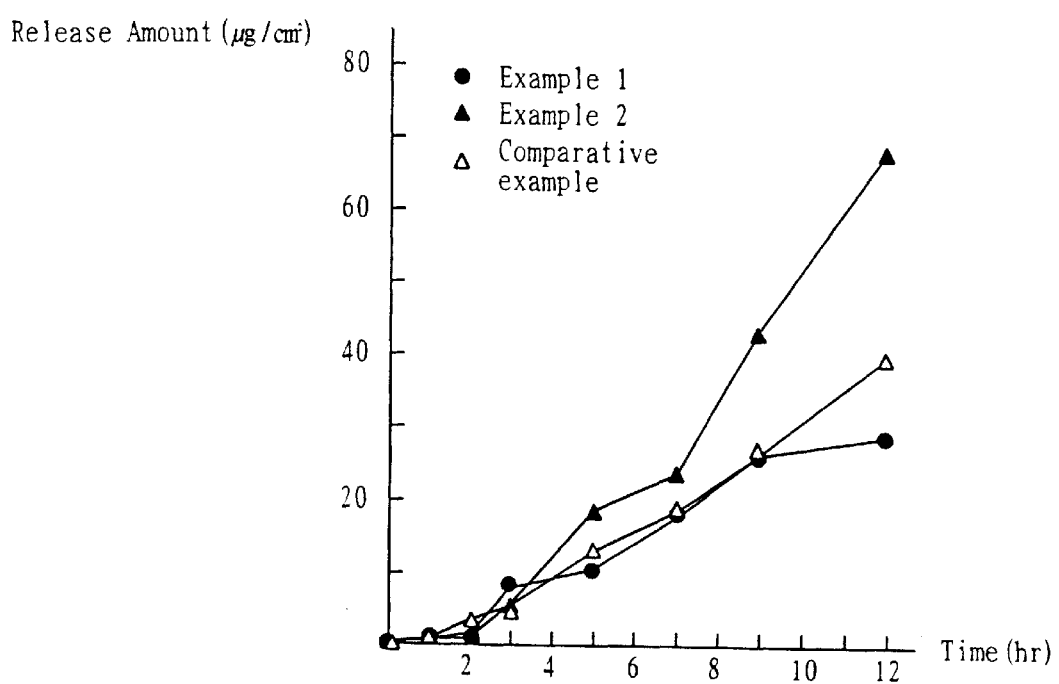
FIG. 2 illustrates graphs for showing release amount of drug with respect to time in the sustained/immediate acting ketoprofen patches prepared through examples 1 and 2, according to the present invention.
Figure 3:
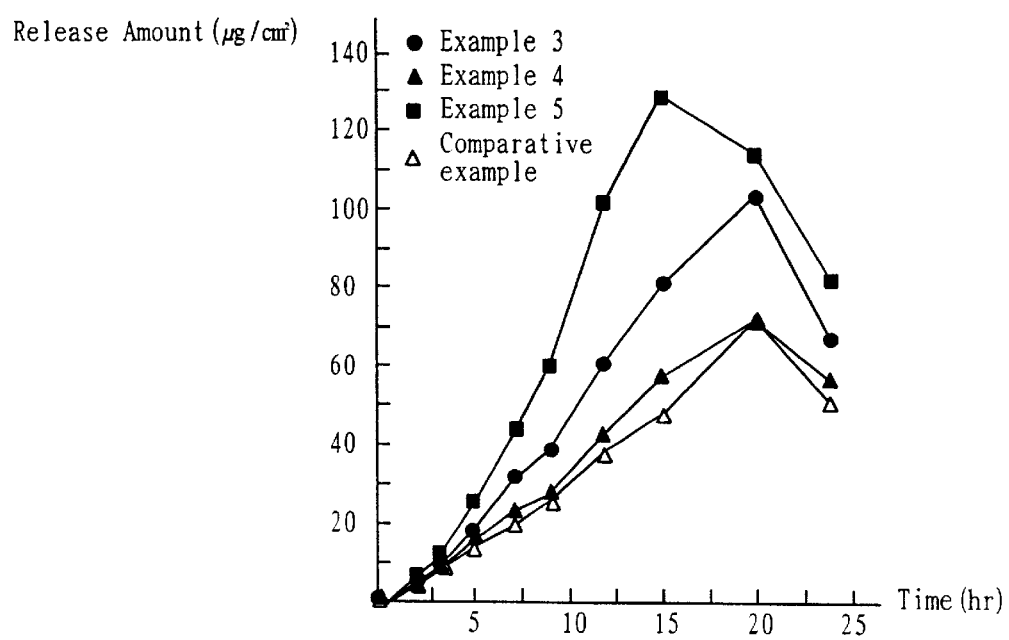
FIG. 3 illustrates graphs for showing release amount of drug with respect to time in the sustained/immediate acting ketoprofen patches prepared through examples 3, 4 and 5, according to the present invention.
Figure 4:
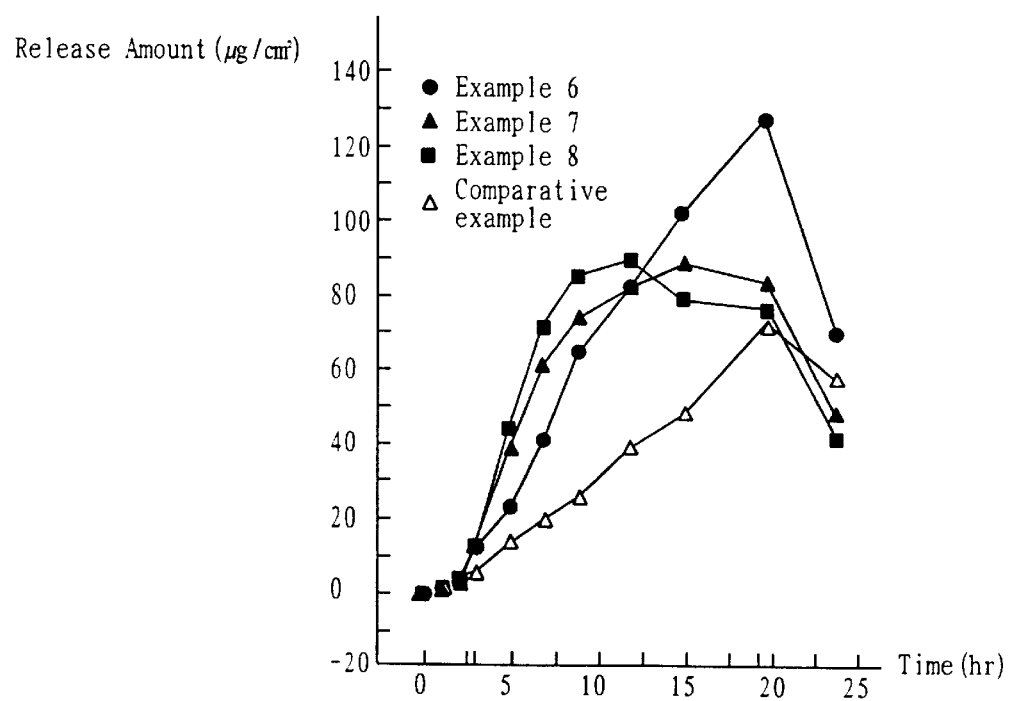
FIG. 4 illustrates graphs for showing release amount of drug with respect to time in the sustained/immediate acting ketoprofen patches prepared through examples 6, 7 and 8, according to the present invention.

In particular, the release amounts of drug using the hairless mouse are illustrated as graphs in FIGS. 2, 3 and 4, for the easy confirmation of the effect according to the present invention with eyes. In FIGS. 2, 3 and 4, release amounts of drug of the control are illustrated as "Δ". "●" and "▲" illustrated in FIG. 2 represent release amounts of drug according to time for the sustained ketoprofen patches manufactured through Examples 1 and 2, and "●", "▲" and "■" in FIG. 3 represent release amounts of drug of the immediate acting ketoprofen patches manufactured through Examples 3, 4 and 5. "●", "▲" and "■" in FIG. 4 represent release amounts of drug of the immediate acting ketoprofen patches manufactured through Examples 6, 7 and 8.

Referring to Table 1, the loading amounts of the drug per area for the ketoprofen patches manufactured by the examples and the control (comparative example) are similar and in the range of 0.71–0.84 mg/1.8361 cm². However, the adhesive strength of the ketoprofen patches manufactured by the examples except that manufactured by example 5 (adhesive strength: 157 g/cm) are superior to that of the control.

In addition, the release amounts of the drug solutions according to the time for the sustained ketoprofen patches according to the present invention are similar with that of the control, as shown in Table 2 and FIGS. 2, 3 and 4. However, when the skin adhesion layer is thin (about 10 μm: example 2), the sustained release of the drug and the release amount of drug according to the time are good. For the immediate acting ketoprofen patches, the initial release amounts of drug are larger than that of the control. In addition, release amounts of drug after 3 hours from the adhesion of the patches to the skin are very good.

As described above, since the ketoprofen patch according to the present invention has the release controlling function for the drug, the effect of a medicine can be durably and homogeneously sustained. And since the adhesiveness to the skin is good, any number of times of attaching and detaching are possible. In addition, the patch adheres closely to the skin and the transferring of the drug through the skin is sufficient. Moreover, the sustained release of drug and the initial release of the drug is good. And, in the present invention, except of drug and enhancer, non-adhesive polymer as binder of drug layer can be used. Accordingly, various polymers can be employed.

While the present invention has been particularly shown and described with reference to the particular embodiments thereof, it will be understood by those skilled in the art that various changes in form and details may be effected therein without departing from the spirit and scope of the invention as defined by the appended claims.

What is claimed is:

1. A ketoprofen patch comprising:
   a moisture permeable backing;
   a moisture non-permeable primer on said backing, said primer being formed of a material selected from the group consisting of an acrylic adhesive and a rubber adhesive;
   a moisture-permeable drug layer containing ketoprofen in a therapeutically effective amount, said drug layer being on said primer and being separated from said backing by at least said primer, wherein said drug layer is a matrix comprising 10–80 wt % of ketoprofen and a mixture of PVA and an acrylic emulsion and at least one compound selected from the group consisting of ethylenevinyl acetate (EVA) emulsion and a synthetic rubber latex based on a total amount of drug solutions; and
   a skin adhesion layer having a release controlling function of a drug solution, said skin adhesion layer having a thickness in the range of between substantially 5 to 40 μm and comprising an acrylic adhesive,
   said drug layer and said adhesion layer being separate layers within a complex laminated structure with said skin adhesion layer on said drug layer.

2. A ketoprofen patch as claimed in claim 1, wherein said primer is manufactured by dissolving acrylic adhesive in ethyl acetate to obtain a solution, coating said solution and onto a silicon coated paper.

3. A ketoprofen patch as claimed in claim 1, wherein said primer is manufactured by coating a mixture prepared by adding a tackifier and an antioxidant to rubber, onto a silicon coated paper.

4. A ketoprofen patch as claimed in claim 1, wherein said drug layer is a matrix comprising 5–95 wt % of a mixture of aqueous poly(vinyl alcohol) (PVA) and acrylic adhesive based on a drug solution.

5. A ketoprofen patch as claimed in claim 1, wherein said drug layer is a matrix comprising 5–95 wt % of a compound and an acrylic adhesive based on a drug solution, wherein said compound is selected from the group consisting of poly(acrylic acid), poly(acryl amide), poly(N-vinyl pyrrolidone), chitin, chitosan, cellulose and a salt thereof.

6. A acting ketoprofen patch as claimed in claim 5, wherein said mixture is obtained by mixing said aqueous PVA and said acrylic adhesive in a ratio of 50:50–75:25 by weight parts based on a solid content.

7. A ketoprofen patch as claimed in claim 1, wherein said mixture is obtained by mixing said PVA and said EVA in a ratio of 30:70–70:30 by weight parts based on a solid content.

8. A ketoprofen patch as claimed in claim 1, wherein said drug layer is a matrix comprising 10–80 wt % of a mixture of PVA, EVA and synthetic rubber latex based on a total amount of drug solution.

9. A ketoprofen patch as claimed in claim 8, wherein said mixture is obtained by mixing said PVA, said EVA and said synthetic rubber latex in a ratio of 10–90:10–90:1–50 by weight parts based on solid contents.

10. A ketoprofen patch as claimed in claim 4 9, wherein said drug layer further comprises at least one enhancer compound selected from the group consisting of lipid acid alcohol, sorbitan monooleate, poly(ethylene glycol), glycerin, pyrrolidon, N-methyl-pyrrolidon, dimethyl formamide, dimethyl sulfoxide and diethyl toluamide as a enhancer of said drug solution.

11. A ketoprofen patch as claimed in claim 10, wherein said lipid acid alcohol is at least one selected from the group consisting of oleyl alcohol and derivatives thereof.

12. A ketoprofen patch as claimed in claim 10, wherein said drug layer includes the enhancer and ketoprofen in a ratio of 100:1–100 by weight parts.

13. A ketoprofen patch as claimed in claim 1, wherein said skin adhesion layer comprises 0.005–50 wt % of at least one emulsifier or organic salt selected from the group consisting of Bile salt, oleyl alcohol, sorbitan monooleate, poly(ethylene glycol), glycerin, pyrrolidon, N-methylpyrrolidon, dimethyl formamide, dimethyl sulfoxide and diethyl toluamide.

14. A ketoprofen patch as claimed in claim 1, wherein thicknesses of said primer, said drug layer and said skin adhesion layer are 20–50 $\mu$m, 10–100 $\mu$m and 5–40 $\mu$m, respectively.

15. A ketoprofen patch as claimed in claim 14, wherein when said drug layer is solid matrix type, said skin adhesion layer does not include drug.

16. A method for manufacturing a ketoprofen patch comprising the steps of:
 a first step of forming a primer by coating an adhesive selected from the group consisting of a rubber adhesive and an acrylic adhesive containing solid matter onto a silicon coated paper, or polyester film, drying and transfer coating onto a backing;
 a second step of forming a drug layer by coating a drug solution onto a silicon coated paper, drying and transfer coating onto said primer, said drug solution being prepared by mixing aqueous polyvinyl alcohol and an acrylic adhesive with at least one compound selected from the group consisting of an ethylene-vinyl acetate copolymer and a synthetic rubber latex to obtain a mixture, and adding to said mixture a solution obtained by dissolving a therapeutically effective amount of ketoprofen powder in at least one enhancer; and
 a third step of forming a skin adhesion layer, having a thickness in the range of between substantially 5 to 40 $\mu$m, by dissolving emulsifier in ethyl-acetate to obtain a solution, mixing said solution with acrylic adhesive, stirring thus obtained mixture, coating said mixture onto a silicon coated paper, drying and transfer coating onto said drug layer.

\* \* \* \* \*